United States Patent [19]

Nowak et al.

[11] Patent Number: 5,547,850
[45] Date of Patent: Aug. 20, 1996

[54] PROCESS FOR DETERMINING HIRUDIN AND SYNTHETIC THROMBIN INHIBITORS

[75] Inventors: Götz Nowak; Elke Bucha; Jutta Hoffman, all of Erfurt, Germany

[73] Assignee: Max-Planck-Gesellschaft, Gottingen, Germany

[21] Appl. No.: 284,453

[22] PCT Filed: Jan. 25, 1993

[86] PCT No.: PCT/EP93/00161

§ 371 Date: Oct. 5, 1994

§ 102(e) Date: Oct. 5, 1994

[87] PCT Pub. No.: WO93/16390

PCT Pub. Date: Aug. 19, 1993

[30] Foreign Application Priority Data

Feb. 11, 1992 [DE] Germany ............... 42 03 980.0

[51] Int. Cl.⁶ .................. C12Q 1/56; C12Q 1/37; G01N 33/00
[52] U.S. Cl. .................. 435/13; 435/23; 436/34; 436/69
[58] Field of Search .............. 435/13, 23, 212; 436/34, 69

[56] References Cited

U.S. PATENT DOCUMENTS

| | | | |
|---|---|---|---|
| 4,334,018 | 6/1982 | Kirchhof | 435/13 |
| 4,379,142 | 4/1983 | Port | 424/101 |
| 5,187,102 | 2/1993 | Stocker | 436/69 |
| 5,192,689 | 3/1993 | Hemker | 436/69 |

FOREIGN PATENT DOCUMENTS

| | | | |
|---|---|---|---|
| 3330699 | 3/1985 | Germany | C12Q 1/56 |
| 9207954 | 5/1992 | WIPO | |

OTHER PUBLICATIONS

Rhee M., Role of Meizothrombin and Meizothrombin (DESFI) . . . Biochem 1982 21 pp. 3437–3443.
Tijburg P., Formation of Meizothrombin . . . J of Biol Chem 266 (6) 1991 p. 4017–4022.
Chemical Abstract 87 (1977): 19602b; Latallo, Z. S.; Teisseyre, E., Proc. Symp. Dtsch. Ges. Klin.
Chem Abstract vol. 98: 13567p 1983 Briet E.
Chemical Abstracts 102 (1985): 125309p; Green, D.; et al.; Thromb. Res. 1985, 37 (1), 145–53.

*Primary Examiner*—Ralph J. Gitomer
*Attorney, Agent, or Firm*—Sughrue, Mion, Zinn, Macpeak & Seas

[57] ABSTRACT

The present invention provides a process for determining the content of hirudin or of a synthetic thrombin inhibitor in the blood. A prothrombin intermediate, or a compound that splits prothrombin into meizothrombin, or a mixture thereof, is added to a blood sample and a measurement is taken of the time that elapses between the addition of the reagent to the sample and the beginning of coagulation. Comparison is then made, where necessary, with a standard calibration curve.

10 Claims, 2 Drawing Sheets

SCHEMATIC OF THE ECARIN-INDUCED PROTHROMBIN ACTIVATION

SCHEMATIC OF THE ECARIN-INDUCED PROTHROMBIN ACTIVATION

PROCESS FOR DETERMINING HIRUDIN AND SYNTHETIC THROMBIN INHIBITORS

BACKGROUND OF THE INVENTION

The invention relates to a process for determining hirudin and synthetic thrombin inhibitors in the blood and a preparation for implementing the process.

Hirudin, which is obtained from the salivary gland of the *Hirudo medicinalis* (leech), is an anticoagulant, whose effect is based on the formation of a chemical compound with thrombin, whereby its catalytic action is inhibited. Hirudin is a miniprotein comprising 65 amino acids with a molecular weight of 7 kD. Owing to its strong affinity for thrombin ($k_1$ values of $10^-$ mol/l) and its direct mechanism of action, it is of great interest. Its clinical application was extremely limited in the past, since hirudin was not easily accessible in the standardized form. Today hirudin can be produced through genetic engineering; and, therefore, its clinical application can be expected in the near future.

For example, pharmaceutical preparations for oral administration are described in the EP-A-0 468 327; said preparations contain recombinant hirudin.

Recently hirudin has been intensively investigated pharmacologically; and the pharmacological data were acquired from experimental animals and humans. Hirudin is not metabolized in the liver, but rather eliminated in an unchanged form through the kidneys. Hirudin has an elimination half-life of about 1 to 2 hours and is distributed into the extracellular fluid spaces of the body. Analogous to heparin, hirudin is not resorbed orally. Past investigations have demonstrated that hirudin is active in almost all models of thrombosis, thus even during endotoxic shock and during experimental cardiac infarction and during prevention of reocclusion following thrombolysis. No immunological reactions were detected in the clinical-pharmacological investigations. During clinical investigations hirudin has proven to be superior to heparin as an anticoagulant and antithrombotic agent.

Currently many research laboratories are working worldwide on synthesizing synthetic, especially small molecular, inhibitors. The synthetic thrombin inhibitors act in the same manner as hirudin. Investigations with derivatives of benzamidines, such as NAPAP (Nα-(2-napthylsulforyl-glycyl)-D,L-amidinophenylalanine-piperidide) and with so called tripeptides have exhibited the most progress. All synthetic thrombin inhibitors are currently in preclinical research. Their effects can be equated qualitatively with those of hirudin. However, the metabolism of the synthetic thrombin inhibitors differs from that of hirudin. Usually the thrombin inhibitors are metabolized in the liver or in the blood. It is anticipated that such substances will be available soon for clinical testing. The advantage over hirudin lies in the fact that the compounds can be administered orally.

However, for proper therapy or prophylaxis it is necessary that the hirudin content and the synthetic thrombin inhibitor content in the blood can be determined continuously, in order to avoid underdosing or to prevent side effects due to overdosing. In other words, therapeutic drug monitoring must be available. To date there exists no process for determining hirudin and synthetic thrombin inhibitors, especially in the blood, that can be implemented in a simple manner.

The present invention is based on the problem of providing a process for determining hirudin and synthetic thrombin inhibitors, especially in the blood, that can be applied extensively in a simple manner in hospitals, medical practices and laboratories and, for example, at the preoperative examination for diagnosing the risk of bleeding or thrombosis, for monitoring the anticoagulant therapy in thrombosis-endangered patients and at the followup of numerous diseases, for example severe infections, liver function damages and malignant diseases.

The process of the invention is supposed to be easy to implement, during which process devices can be used that already exist in hospitals and medical practices. In addition, a preparation for implementing the process shall be made available.

SUMMARY OF THE INVENTION

The subject matter of the invention is a process for determining hirudin or synthetic thrombin inhibitors in the blood, wherein a prothrombin intermediate, a compound that splits prothrombin into meizothrombin, a salt thereof or a mixture of these compounds, and optionally buffers and/or other customary additives are added to the blood; and the time that elapses starting from the addition to the start of coagulation is measured, whereby meizothrombin, PIVKA meizothrombin or meizothrombin-des-fragment-1 is used as the prothrombin intermediate.

The subject matter of the invention is also a preparation for implementing the aforementioned process, which is characterized in that it contains a prothrombin intermediate that is defined above, a compound that splits prothrombin into meizothrombin, a salt thereof or a mixture of these compounds together with heparin and buffers and/or other conventional additives.

DETAILED DESCRIPTION OF THE INVENTION

Figure 1:
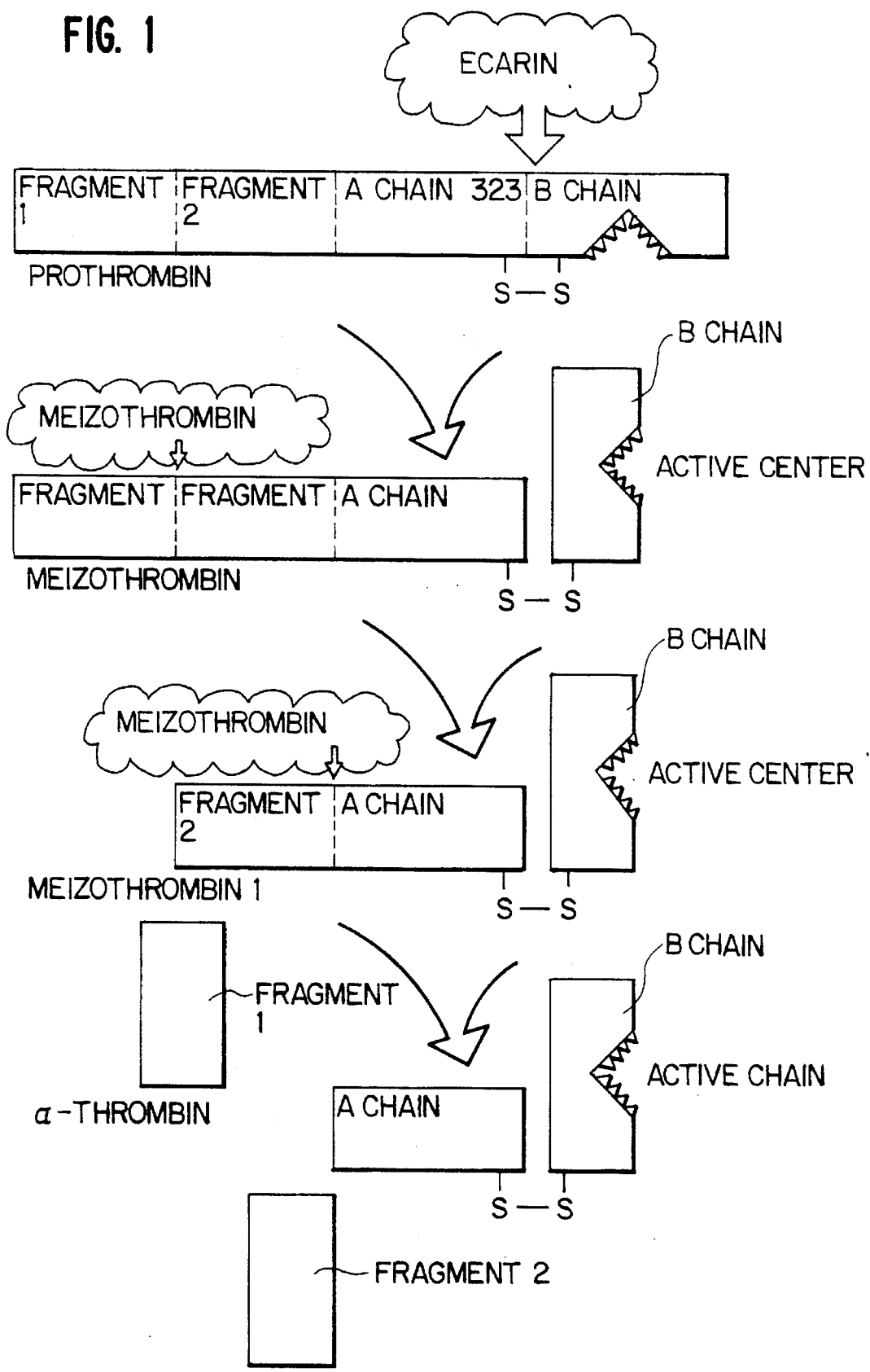
FIG. 1 of the drawing is a schematic of prothrombin activation induced by ECARIN.

The process according to the invention has the significant advantage that it can be implemented in a simple manner and that the results of the tests are rapidly available, since they can be read off calibration curves. The process can be implemented simply on a large scale in hospitals, medical practices and laboratories and does not required any especially trained personnel.

The process according to the invention can be implemented for determining hirudin or synthetic, preferably small molecular, thrombin inhibitors. Examples of synthetic thrombin inhibitors are above all the derivatives of tripeptide phe-pro-arg, like boric acid derivatives, argininals, chloromethylketone derivatives and derivatives that are modified at the amino acids, and benzamidine derivatives and also so called hirologs, i.e. synthetic hirudin-analogous partial sequences. The antidote principle is the same as for hirudin.

The scientific background of this method is based on the interaction of hirudin or synthetic thrombin inhibitors with a prothrombin intermediate, like intermediary meizothrombin, an intermediate product of prothrombin-thrombin conversion, or meizothrombin-des-fragment-1. This conversion involves a multistepped reaction, wherein very specific protein bonds are dissolved by means of limited proteolytic reaction steps. Normally during activation of the coagulation cascade a proteolytically active complex is formed from the activated factor V, Ca++, phospholipid and factor X, which initiates the prothrombin-thrombin conversion. The result is only small quantities of intermediates of factor II, because the prothrombin is activated quasi "solid-phase like" at this prothrombin complex. If, however, the coagulation is initiated with a specific fraction of a snake venom, e.g. from *Echis-carinatus*, then "atypical" intermediates, e.g. meizothrombin, PIVKA meizothrombin or meizothrombin-desfragment-1, are formed predominantly from prothrombin. These intermediates are inactivated by means of hirudin or synthetic thrombin inhibitors, but not by means of heparin. Thus, it is possible to set up a coagulation test, in which meizothrombin or PIVKA meizothrombin that is inactivated by means of the hirudin contained in the sample is produced in the blood or in a component of the blood by means of a snake venom, for example Echis snake venom. The affinity of hirudin and synthetic thrombin inhibitors for the prothrombin intermediates is very high. For meizothrombin it is, for example, $k_1 > 10^{-10}$ mol/l, so that free prothrombin intermediate, for example meizothrombin, is not produced until the hirudin or the synthetic thrombin inhibitors have been totally consumed. This prothrombin intermediate, for example meizothrombin, can convert the fibrinogen contained in the sample into fibrin. This formation of fibrin is documented in time by means of coagulating the sample. The quantification is done in that the hirudin content of the blood sample extends linearly the coagulation time in the therapeutic blood level range and thus allows a fast and effortless statement.

In the process according to the invention the time that elapses from the addition of the compound to the blood up to the start of coagulation is measured. Numerous methods are known for measuring the start of coagulation. Most often a small platinum hook, which pulls a fibrin thread out of the solution when clots form, is inserted periodically in the coagulation batch. This instant is then registered as the coagulation end point. The registration process can be done manually by means of a stop watch or electrically by triggering a contact, when the platinum hook is designed as an electrode. Moreover, there are automated methods.

The process according to the invention has the big advantage that the adaptation to all measuring principles of coagulation diagnostics, especially to automated methods, is possible. When chromogene thrombin substrates are added to suitable plasma samples, the measurement can be made in automatic laboratory equipment.

The process according to the invention can be implemented in a simple manner and allows the hirudin content to be read at a calibration curve. The process according to the invention can be implemented with total blood, blood plasma, but also with body fluids, like urine, compressed tissue fluid or cell eluation following homogenization, to which a quantity of normal plasma is added. The process according to the invention has the significant advantage that the blood can still contain heparin, since heparin does not disturb the process.

According to the invention, meizothrombin, PIVKA prothrombin or meizothrombin-des-fragment-1 is used, for example, as the prothrombin intermediate. Meizothrombin is commercially available and can be obtained from the Pentapharm company in Switzerland. However, meizothrombin, PIVKA-prothrombin or other prothrombin intermediates can also be formed in vitro.

As shown in the following diagram, four factors of the coagulation system—factor II (prothrombin), factor VII, factor IX and factor X—are characterized in that they contain gamma-carboxyglutamic acid groups. This gamma-carboxylation at the glutamic acid does not take place until after the ribosomal synthesis of the "acarboxy factor" in the liver with the aid of an enzyme system, which requires vitamin K as the cofactor The gamma-carboxyglutamic acid groups are essential for the coagulation action. They represent the necessary bonding valences for calcium ions. For treatment with indirect anticoagulants of the Dicumarol type ("vitamin K antagonists"), the postribosomal gamma-carboxylation cannot take place; and the blood exhibits incomplete coagulation factors or acarboxy factors, because they lack the calcium-binding gamma-carboxy groups. These coagulation factors are also called PIVKA factors (PIVKA=proteins induced by vitamin K antagonists).

When Ecarin is added to the plasma of patients treated with such anticoagulants of the Dicumarol type, PIVKA meizothrombin is produced in this plasma from the PIVKA prothrombin in the same manner through a limited proteolysis as is also the case in normal plasma samples with prothrombin.

This PIVKA meizothrombin or other PIVKA intermediates have retained their ability to bond with hirudin, but they have no or significantly less effects on other factors of the coagulation cascade (platelets, fibrinogen, thrombomodulin etc.). According to the invention, meizothrombin, PIVKA meizothrombin, their intermediates and PIVKA intermediates from PIVKA prothrombin can be used. They can originate from humans or from other mammals.

To prepare meizothrombin, immobilized Ecarin can be packed, for example, in mini columns ranging in size from 2–4 cm³ for example. Ecarin immobolizate (Pentapharm AG, Basel) is afforded in the swollen state, suspended in an aqueous solution of sodium chloride 0.15 M, sodium acetate 0.02 M, Prionex (R) (trademark of Pentapharm AG from a protein-stabilizing polypeptide fraction from cleaned pig skin collagen) 0.2% and trichloroisobutanol 0.3%, pH 5.5. One gram of swollen Ecarin immobilizate produces from barium citrate eluate at 37° C., pH 8.4, within 30 minutes 500 to 700 U amidolytic activity (1 U=123 NIH units), measured at tos-gly-pro-arg-pNA (Chromozym (R) TH).

Then purified prothrombin fractions are put on these columns; and the formed meizothrombin, optionally following stabilization with heparin, is subsequently freeze-dried. The freeze-dried material can be packed into ampoules and then reconstituted with a suitable solvent for the application.

To prepare meizothrombin-des-fragment-1, the same process as for meizothrombin is used. In the batch process only a longer reaction time (3–4 hours) has to be planned. Meizothrombin-des-fragment-1 is a product following the activation of meizothrombin.

According to the invention, a snake venom is used as the compound that splits prothrombin into meizothrombin. Examples of snake venom are Ecarin and poisons from Dispholidus, Rhabdophis, Bothrops, Notechis, Oxyuranus and Russel viper types. The snake venoms, like Ecarin and immobilized Ecarin, are commercially available and can be acquired, for example, from the Pentapharm company in Switzerland.

According to the invention, preferably Ecarin, a highly purified fraction of Echis-carinatus toxin, is used as the snake venom. Ecarin splits a peptide bond at arginine 232 of the prothrombin, producing the intermediate meizothrombin. Normally the additional reaction occurs through autocatalysis or through thrombin acceleration. When hirudin is present in the blood, the meizothrombin and hirudin interact. In contrast, heparin cannot react with meizothrombin. The attached FIG. 1 shows these actions.

Figure 2:
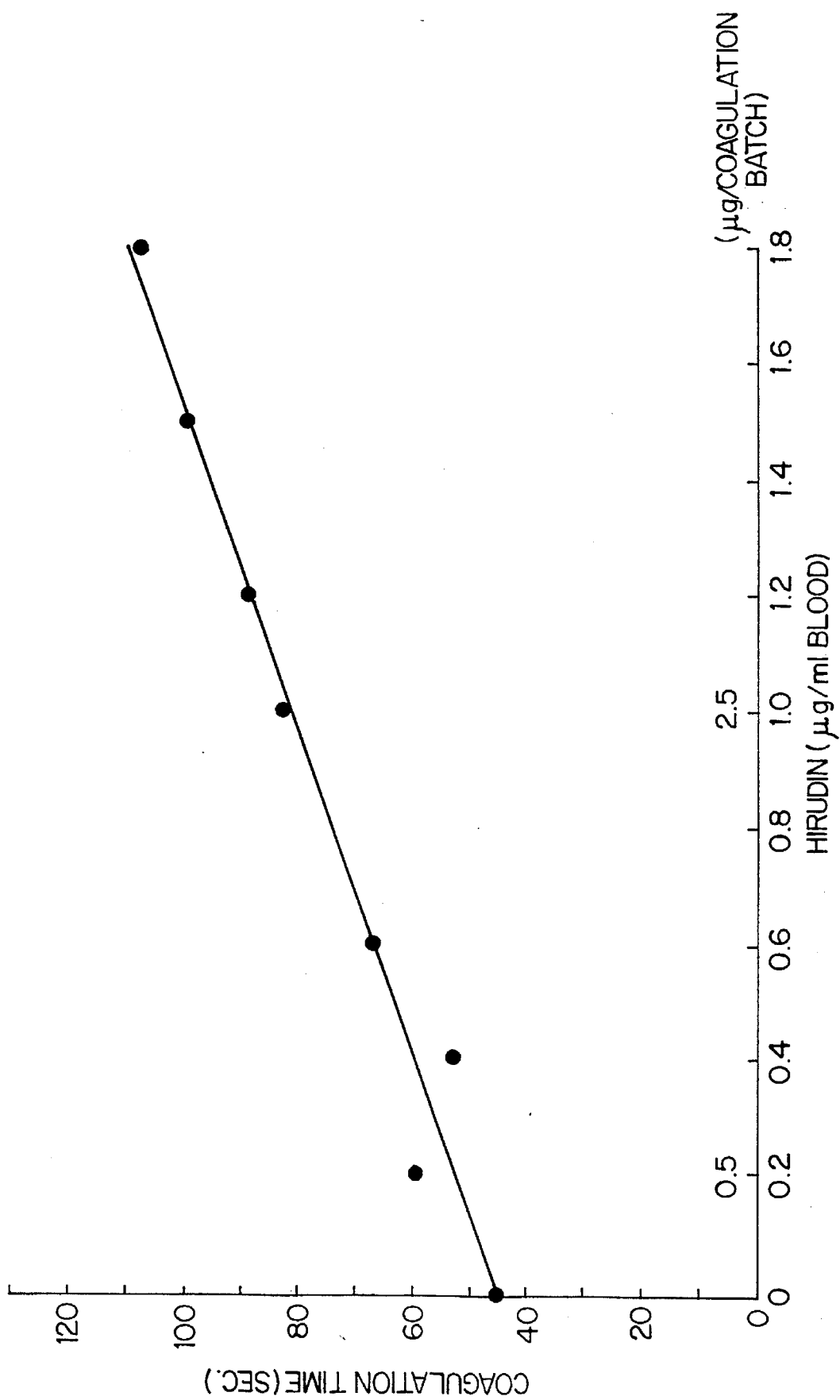
FIG. 2 of the drawing illustrates a calibration curve plotting coagulation time against increasing amounts of hirudin.

The procedure for determining the hirudin content in the blood is as follows. 0.16 ml of buffer, 0.02 ml of 0.1 M $CaCl_2$ solution and 0.02 ml of Ecarin (200 EU/ml) are added to 0.4 ml of heparin blood (20 IE heparin/ml blood). The start of coagulation is determined by means of mechanical, automatic coagulation time measurement. To plot a calibration curve, increasing amounts of hirudin are added into the buffer portion of the coagulation charge. It is apparent from the attached FIG. 2 that there is linearity over a concentration range of 0.1–2 μg hirudin/coagulation batch. Thus, very fast statements about the hirudin content of a blood sample is possible. Another advantage lies in the use of whole blood. The total measurement time is at about 5 minutes optimal for a therapeutic drug monitoring, in the sense of a bedside diagnostic.

The following example explains the invention.

In the following test example a coagulation time measuring device was used, in which the start of coagulation is detected with a magnet in the coagulation batch by means of disturbances in the electric field while the sample tube is rotating. Thus, whole blood is used as the sample batch. The "blood coagulation timer" Hemochron (R) model 801 of Int. Technidyne Corp. Edison, N.J., U.S.A. has two test channels and thus allows double determinations without any problems.

EXAMPLE

In the Hemochron test tube of P214 model 0.02 ml $CaCl_2$ 0.1 M 0.02 ml Ecarin 200 EU/ml NaCl 0.16 ml tris-buffer 0.05 M pH 7.4 at 37° C.

0.40 ml test blood are mixed, the time is started, the test tube is put into the automatic coagulation device and the time for the start of coagulation is registered. The procedure is identical for plotting a calibration curve, from which the hirudin concentration at suitable coagulation time can be read. In so doing, defined amounts of hirudin and untreated blood, instead of test blood, are added to the buffer. The coagulation time is extended as the concentration of hirudin increases.

The following values were determined for four subjects by means of double determination.

|   | coagulation time [sec] | hirudin/coagulation batch [μg] | hirudin/ml blood [μg] |
|---|---|---|---|
| subject A | (70; 63) φ 66.5 | 0.5 | 1.25 |
| subject B | (79; 86) φ 82.5 | 0.9 | 2.25 |
| subject C | (46; 50) φ 48.0 | 0.1 | 0.25 |
| subject D | (44; 48) φ 46.0 | 0.0 | 0.00 |

It is apparent that for subject D there is an underdose or a consumption of hirudin. For subjects C and A the hirudin blood level is in the therapeutic range and for subject B in the toxic range.

We claim:

1. A process for determining a concentration of hirudin or of a synthetic thrombin inhibitor selected from the group consisting of a derivative of a tripeptide phe-pro-arg and a hirolog in blood, in a blood component or in a body fluid other than blood, comprising adding a material selected from the group consisting of (1) a prothrombin intermediate selected from the group consisting of meizothrombin, PIVKA meizothrombin, PIVKA being an abbreviation for protein induced by vitamin K antagonist, and meizothrombin-des-fragment-1 or a pharmaceutically acceptable salt of said prothrombin intermediate, (2) a compound that splits prothrombin into meizothrombin or a pharmaceutically acceptable salt of said compound and (3) a mixture of said compound that splits prothrombin into meizothrombin or a salt thereof and said prothrombin intermediate or a salt thereof, to the blood, blood component, or a body fluid other than blood, measuring an elapsed time between said adding and the start of coagulation in said blood, blood component or a body fluid other than blood and comparing the elapsed time measurement with a standard in order to determine said concentration.

2. The process of claim 1, wherein the blood or the blood component or other body fluid contains heparin.

3. The process of claim 1 or claim 2, wherein the compound that splits prothrombin into meizothrombin is a snake venom or purified fraction thereof.

4. The process of claim 3, wherein the purified fraction of snake venom is ecarin.

5. The process of claim 1, wherein the concentration of hirudin is determined.

6. The process of claim 1, wherein the concentration of a synthetic thrombin inhibitor is determined.

7. The process of claim 1, wherein the elapsed time measured is compared with a standard which is a calibration curve to determine the concentration of the hirudin or of the synthetic thrombin inhibitor.

8. A diagnostic composition for determining the concentration of hirudin or of a synthetic thrombin inhibitor selected from the group consisting of a derivative of a tripeptide phe-pro-arg and a hirolog in blood, a blood component or a body fluid other than blood comprising a material selected from the group consisting of (1) a prothrombin intermediate selected from the group consisting of meizothrombin, PIVKA meizothrombin wherein PIVKA is an abbreviation for protein induced by vitamin K antagonist, and meizothrombin-des-fragment-1 or a pharmaceutically acceptable salt of said prothrombin intermediate, (2) a compound that splits prothrombin into meizothrombin or a pharmaceutically acceptable salt of said compound and (3) a mixture of said prothrombin intermediate or salt thereof and said compound that splits prothrombin into meizothrombin or said salt thereof, and a pharmaceutically acceptable diluent.

9. The diagnostic composition of claim 18, wherein the compound that splits prothrombin into meizothrombin is a snake venom or a purified fraction thereof.

10. The diagnostic composition of claim 9, wherein the purified fraction of snake venom is ecarin.

* * * * *